(12) United States Patent
Coroneo

(10) Patent No.: US 8,216,306 B2  
(45) Date of Patent: Jul. 10, 2012

(54) OCULAR AUTO-FOCUSING LENSES

(76) Inventor: Minas Theodore Coroneo, Sydney (AU)

(*) Notice: Subject to any disclaimer, the term of this patent is extended or adjusted under 35 U.S.C. 154(b) by 1302 days.

(21) Appl. No.: 11/332,088

(22) Filed: Jan. 13, 2006

(65) Prior Publication Data

US 2006/0155372 A1     Jul. 13, 2006

Related U.S. Application Data (60) Provisional application No. 60/644,249, filed on Jan. 13, 2005.

(51) Int. Cl.  
*A61F 2/16* (2006.01)

(52) U.S. Cl. .................. 623/6.22; 623/6.13; 623/6.37

(58) Field of Classification Search ............... 128/898; 623/4.1, 6.11, 6.13, 6.22, 6.34, 6.37, 6.56  
See application file for complete search history.

(56) References Cited

U.S. PATENT DOCUMENTS

| | | | | |
|---|---|---|---|---|
| 4,718,906 A | * | 1/1988 | Mackool | 623/6.21 |
| 5,712,721 A | * | 1/1998 | Large | 359/245 |
| 7,041,133 B1 | * | 5/2006 | Azar | 623/6.22 |

FOREIGN PATENT DOCUMENTS

| | | |
|---|---|---|
| WO | WO 98/02143 | 1/1998 |
| WO | WO 99/18456 | 4/1999 |
| WO | WO 03/069380 A1 | 8/2003 |
| WO | WO 03069380 A1 * | 8/2003 |

* cited by examiner

*Primary Examiner* — David H Willse  
*Assistant Examiner* — Javier Blanco  
(74) *Attorney, Agent, or Firm* — Knobbe Martens Olson & Bear LLP

(57) ABSTRACT

The present invention relates to an ocular, variable-focus lens, and in particular, to an ocular, fluid-focussed, accommodating lens having first and second fluids which are in contact over a meniscus of changeable shape, for the restoration or improvement of vision in a patient.

25 Claims, 2 Drawing Sheets

OCULAR AUTO-FOCUSING LENSES

RELATED APPLICATIONS

This application is a non-provisional application of Provisional Application No. 60/644,249, filed Jan. 13, 2005, the entire disclosure of which is expressly incorporated herein by reference in its entirety.

FIELD OF THE INVENTION

The present invention relates to an ocular, variable-focus lens, and in particular, to an ocular, fluid-focussed, accommodating lens having first and second fluids which are in contact over a meniscus of changeable shape, for the restoration or improvement of vision in a patient.

DESCRIPTION OF THE RELATED ART

Surgery of the crystalline lens has advanced considerably over the last two decades, with considerable research being channeled into methods such as phacoemulsification and other methods for surgical removal of the lens, particularly when it is cataractous.

Intraocular lens replacement surgery has become a widespread procedure, particularly for increasingly common conditions such as cataracts, as well as rarer conditions or situations such as aphakia (e.g. congenital aphakia) and acquired aphakia such as caused by trauma. Even more recently, clear-lens replacement (CLR) procedures, which involve removal of a patient's own (clear, non-cataractous) lens and replacement with an artificial lens, have become available as an alternative for patients considering refractive surgery to decrease dependence on contact lenses and eyeglasses, in conditions such as myopia and hypermetropia. Such CLR procedures allow an improved refractive advantage over the patient's own lens, however, the patient is subsequently unable to accommodate their vision to close distances unless evolving multifocal or mechanically accommodating intraocular lenses are used.

Accordingly, CLR is best suited for patients over the age of 40 years, and who wear bifocal visual enhancement means (i.e., spectacles or contact lenses). One potential solution to this problem of accommodative loss is implantation of a multifocal intra-ocular lens implant, which works via a series of optical zones that mimic the eye's natural ability to provide near, intermediate and distance vision. This implant allows focusing at both near and far distances, thus allowing most patients to read small size print and drive a car without eyeglasses, following implantation of the lens in both eyes. However, the CLR procedure and multifocal intraocular lens implant are expensive, with the multifocal intraocular lens being particularly complicated to manufacture. Furthermore, significant drawbacks of this lens are that approximately 15% of patients experience "halos" surrounding objects in the visual pathway, and 11% have severe difficulty with glare. Hinged, accommodating lenses such as the Crystalens have also been developed and used with varying degrees of success.

Occasionally the crystalline human lens is replaced in cases of acute glaucoma, since the lens grows in size with increasing age and in some patients pushes the iris forward, obstructing the drainage angle of the eye, resulting in elevated intraocular pressure.

Prosthetic intraocular lenses are typically about 6 mm in diameter, and are provided as one-piece, foldable acrylic, silicone or polycast polymethylmethacrylate lenses, which are surgically implanted into the approximately 10 mm-diameter, capsular bag of the lens. The capsular bag is a relatively inert support structure for such lenses, thus allowing long-term implantation of artificial lenses without inflammatory responses. The lenses are centered in the capsular bag by attached, flexible loops known as haptics.

Less severe visual problems (e.g. long- and short-sightedness) can be corrected by way of placement of contact lenses over the anterior corneal surface, or by wearing eyeglasses. Contact lenses are available as extended-wear or disposable soft lenses, which serve as an alternative to the wearing of spectacles. Rigid contact lenses provide an alternative to these softer lenses, and are able to actually correct certain vision defects. Newer technologies include permanently implanted contact lenses, which allow patients to avoid the day-to-day care required with wearing and storage of disposable and extended-wear contact lenses. Patients who choose to wear eyeglasses often experience discomfort from the pressure of the glasses, and other problems, such as fogging of the eyeglasses, can frequently occur.

Contact lenses and eyeglasses also suffer the drawback of having to be replaced when a patient's vision alters (e.g. worsens with age).

As such, regardless of the currently available technologies for intraocular lens replacement, eyeglasses and contact lens vision correction, the lenses provided for patients do not provide significant improvements to visual acuity, as they have limited focal length, adjustment and power.

SUMMARY OF THE INVENTION

The present invention is based on the finding that patients with vision disorders, and in particular, disorders involving the crystalline lens of the eye, can benefit from highly modified lenses originally developed specifically for use in image-capturing devices such as cameras. In particular, these modified lenses for ophthalmic use are variable fluid focus lenses, which have been developed by the present inventor for use in, on or near the eye of the patient, for the restoration or enhancement of the patient's vision.

Accordingly, in a first broad form, the present invention relates to a method of treating a vision disorder in a patient, the method comprising the placement of a fluid-focussed, accommodating lens on, in or near an eye of the patient, wherein the lens comprises:
  a substantially cylindrical fluid chamber having a cylinder wall and an axis, the fluid chamber including a first fluid and an axially displaced second fluid, the fluids being non-miscible, in contact over a meniscus and having different indices of refraction,
  a fluid contact layer arranged on the inside of the cylinder wall,
  a first electrode separated from the first fluid and second fluid by the fluid contact layer,
  a second electrode acting on the second fluid,
  the fluid contact layer having a wettability by the second fluid which varies under the application of a voltage between the first electrode and the second electrode, such that meniscus shape varies in dependence on the voltage,
  wherein the wettability of the fluid contact layer by the second fluid is substantially equal on both sides of the intersection of the meniscus with the contact layer when no voltage is applied between the first and second electrodes.

In one embodiment, the fluid-focussed, accommodating lens is placed inside a capsular bag of the eye of the patient.

Preferably, the lens is inserted into the capsular bag through a first aperture made by an incision into the eye.

In a particularly preferred form, the incision into the eye is a corneo-limbal incision.

Preferably, the anterior chamber of the eye is maintained by way of an ophthalmic viscoelastic device (OVD).

In a particularly preferred form, the viscoelastic device is inserted into the anterior chamber of the eye, where it maintains a space inside the anterior chamber, and protects the corneal endothelium.

Also preferably, where the lens is placed in the capsular bag of the eye, an opening is made in the lens capsule.

Preferably, the opening in the lens capsule is a capsulorhexis incision.

Even more preferably, the capsulorhexis incision is 4-6 mm in diameter.

In a further preferred form, the content of the lens capsule is removed by way of a phacoemulsification technique.

In yet another preferred form, the lens is held in place within the capsular bag by way of a securing device.

Preferably, the securing device is at least one haptic.

Also preferably, an OVD viscoelastic substance is injected into the capsular bag, thereby reinflating the capsular bag.

In a further form, the fluid-focussed, accommodating lens is placed on the surface of the patient's eye as a contact lens.

In yet a further form, the fluid-focussed, accommodating lens is placed near the patient's eye as eyeglasses.

In a particularly preferred form, a range finder is placed in communication with the fluid-focussed, accommodating lens, the range finder controlling the focal length of the lens.

Preferably, the range finder includes at least one component selected from the group comprising a power source and at least one autofocusing sensor.

In a preferred form, the range finder is internal to the eye.

In another preferred form, the range finder is external to the eye.

In yet another preferred form, the range finder has components that are internal and external to the patient's eye.

In one form, the range finder is provided by two semicircular structures that attach to a peripheral region of an optical zone of the fluid-focussed, accommodating lens.

Preferably, the first semicircular structure contains the at least one autofocusing sensor.

Even more preferably, the first semicircular structure is located inferiorly of the fluid-focussed, accommodating lens.

In another preferred form, the second semicircular component of the range finder provides the power source, and a control unit, the control unit controlling the amount of electrical current delivered to the fluid-focussed, accommodating lens.

In yet another preferred form, the second semicircular component of the range finder is placed along a superior aspect of the fluid-focussed, accommodating lens, according to an in situ position of the lens.

Preferably, the range finder is inserted post-operatively of the fluid-focussed, accommodating lens.

Even more preferably, the power source of the range finder is a battery.

Preferably, the battery is a long-life battery.

Even more preferably, the battery is a rechargeable battery.

In a further preferred form, the rechargeable battery is recharged by electromagnetic induction.

In another preferred form, the control unit is adjustable.

Preferably, the control unit is adjustable by way of radiofrequency signals directed at the control unit.

Even more preferably, electrical coupling of the range finder and the lens is performed prior to closure of a surgical incision for insertion of the range finder.

Preferably, further adjustment of electrical coupling between the range finder and the fluid-focussed, accommodating lens is performed in a post-operative period to set the power of the lens for the patient's eye, further wherein the range of required focusing power of the lens is also adjusted.

Preferably, where the fluid focussed, accommodating lens is a contact lens, the diameter of the contact lens is in a range of approximately 9 to 12 millimeters.

Even more preferably, an outer 2 millimeters of the contact lens contains a range finder.

Preferably, the range finder comprises a power source, at least one autofocusing sensor and a control unit.

Even more preferably, the power source is placed superiorly of the lens in an in situ position.

In yet another preferred form, the at least one autofocusing sensor is placed inferiorly of the lens in an in situ position.

In a further preferred form, the contact lens is positioned on the patient's eye by ballasting.

In another broad form, the present invention relates to a fluid-focus, accommodating lens, the lens comprising:
 a substantially cylindrical fluid chamber having a cylinder wall and an axis, the fluid chamber including a first fluid and an axially displaced second fluid, the fluids being non-miscible, in contact over a meniscus and having different indices of refraction,
 a fluid contact layer arranged on the inside of the cylinder wall,
 a first electrode separated from the first fluid and second fluid by the fluid contact layer,
 a second electrode acting on the second fluid,
 the fluid contact layer having a wettability by the second fluid which varies under the application of a voltage between the first electrode and the second electrode, such that meniscus shape varies in dependence on the voltage,
 wherein the wettability of the fluid contact layer by the second fluid is substantially equal on both sides of the intersection of the meniscus with the contact layer when no voltage is applied between the first and second electrodes,
 wherein the lens is adapted for use in the restoration or enhancement of vision in a patient, and is suitable for placement in, on or near the patient's eye.

Preferably, the lens is an intraocular lens and even more preferably, the lens has an optical zone in a range of approximately 4 to 6 millimeters.

In another preferred form, the lens is adapted for use in a contact lens.

In yet a further preferred form, the lens is adapted for use in eyeglasses.

Preferably, the lens further comprises a range finder.

In a preferred form, the range finder includes at least one component selected from the group comprising a power source, at least one autofocusing sensor, and a controller.

Preferably, the range finder is placed in communication with the fluid-focussed, accommodating lens, where the range finder controls the focal length of the lens.

Where the fluid-focussed, accommodating lens is an intraocular lens, preferably the range finder is provided by first and second semicircular structures that attach to the periphery of the optical zone of the fluid-focussed, accommodating lens.

In this form, it is preferable that the range finder is inserted post-operatively of the fluid-focussed, accommodating lens.

Preferably, the first semicircular structure contains the at least one autofocusing sensor.

Even more preferably, the first semicircular structure is located inferiorly of the fluid-focussed, accommodating lens, in an in situ position.

In another preferred form, the second semicircular component of the range finder provides a power source, and a control unit, the control unit controlling an electrical current from the power source to the fluid-focussed, accommodating lens.

In a further preferred form, the power source is a battery.

Preferably, the battery is a long-life battery.

In another preferred form, the battery is a rechargeable battery.

Preferably, the rechargeable battery is recharged by electromagnetic induction.

In another preferred form, the second semicircular component of the range finder is placed along a superior aspect of the fluid-focussed, accommodating lens.

In a further preferred form, electrical coupling of the range finder and the lens is performed prior to closure of a surgical incision for insertion of the range finder.

Preferably, further adjustment of electrical coupling between the range finder and the fluid-focussed, accommodating lens is performed in a post-operative period to set the power of the lens for the patient's eye, further wherein the range of required focusing power of the lens is also adjusted.

Where the fluid-focussed, accommodating lens is a contact lens, preferably the visual region of the contact lens is between a range of 7 to 12 millimeters, and even more preferably, the range finder is located in a region circumferentially extending beyond a visual region of the contact lens.

Preferably, the width of the circumferentially extending region is approximately 2 millimeters.

Even more preferably, the battery and controlling unit sit superiorly relative to the in situ position of the contact lens.

In a further preferred form, the at least one autofocusing sensor sits inferiorly relative to an in situ position of the contact lens.

BRIEF DESCRIPTION OF THE DRAWINGS

FIG. 1.(A) Schematic diagram of eye with normal lens. (B) Schematic diagram of fluid-focussed, accommodating lens in a capsular bag of an eye.

DETAILED DESCRIPTION OF THE PREFERRED EMBODIMENT

Figure 1:
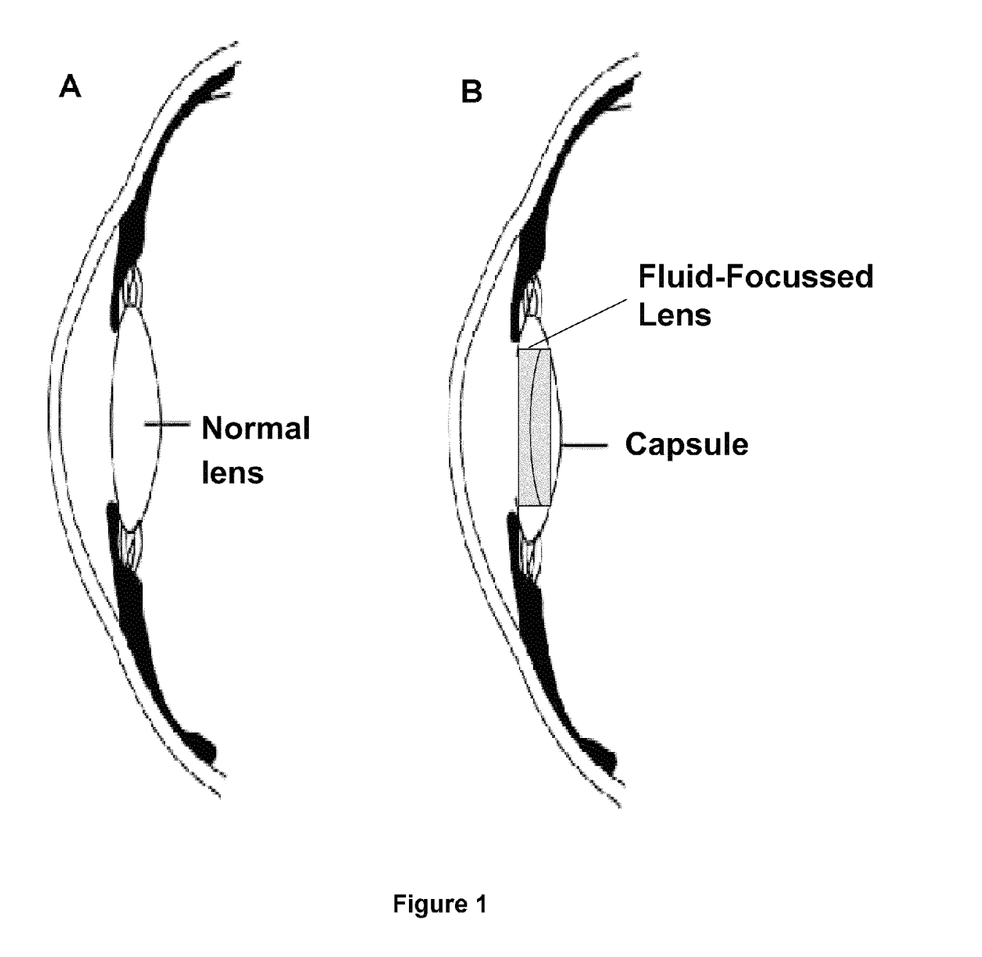
Figure 2:
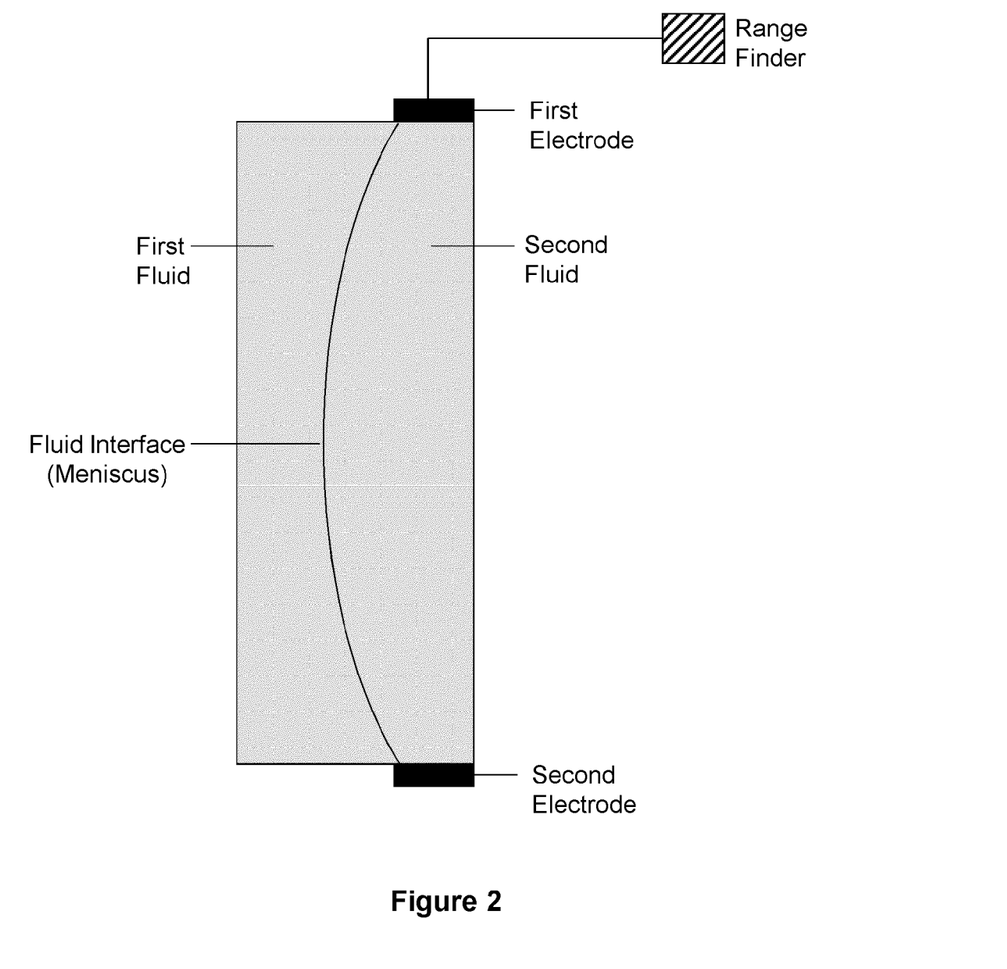
FIG. 2. Schematic cross section of a fluid-focussed, accommodating lens showing first and second fluids, a meniscus at the fluid interface, first and second electrodes, and a range finder.

Throughout this specification, unless the context requires otherwise, the words "comprise," "comprises" and "comprising" will be understood to imply the inclusion of a stated step or element or group of steps or elements but not the exclusion of any other step or element or group of steps or elements.

The present invention relates to the use of a fluid-focussed, accommodating lens in the restoration or enhancement of vision in a patient suffering from a vision disorder. The term "vision disorder" as used herein refers to any condition that adversely affects the patient's own state of refraction, and renders a patient's unaided visual acuity less than 20/20. The term encompasses conditions that include, but are not limited to, cataract, myopia, hypermetropia, astigmatism and aphakia.

The term "patient" refers to patients of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

The fluid-focussed, accommodating lens is referred to herein as comprising a first and second fluids retained in a cylindrical receptacle having transparent circular ends, in which the two fluids are contact over a meniscus, and where the fluids can alter their shapes in response to a small electrical current.

The term "fluids" as used herein refers to a substance that alters its shape in response to any force, and which has a tendency to flow or to conform to a receptacle in which it is placed, and encompasses gases, liquids and mixtures of solids and liquids that are capable of exhibiting flow.

Preferably, the two fluids differ in that one is aqueous or semi-aqueous, and the other non-aqueous (e.g. oil). The cylindrical receptacle walls are coated with a water-repellent coating, thus causing the aqueous or semi-aqueous fluid to form itself into a hemispherical shape. An electrical charge on the sides of the receptacle (i.e. across the water-repellent coating) causes the aqueous fluids to be drawn to the edges of the receptacle, with the other fluid filling up the remaining space in the receptacle, and making the meniscus between the two fluids flatter. This process is generally referred to as "electrowetting", and it permits adjustments of the liquid's surface tension, changing the radius of curvature in the meniscus and thereby the focal length of the lens. Manipulation of the intensity of the current thus allows the interface between the fluids to function as a lens with a highly variable focal length.

Suitable lenses in this regard are described by WO 98/02143, WO 99/18456 and WO 03/069380, the contents of which are herein incorporated by reference. In particular, WO 03/069380 describes a variable focus lens having the following characteristics:

a substantially cylindrical fluid chamber having a cylinder wall and an axis, the fluid chamber including a first fluid and an axially displaced second fluid, the fluids being non-miscible, in contact over a meniscus and having different indices of refraction, a fluid contact layer arranged on the inside of the cylinder wall, a first electrode separated from the first fluid and second fluid by the fluid contact layer, a second electrode acting on the second fluid, the fluid contact layer having a wettability by the second fluid which varies under the application of a voltage between the first electrode and the second electrode, such that meniscus shape varies in dependence on the voltage, wherein the wettability of the fluid contact layer by the second fluid is substantially equal on both sides of the intersection of the meniscus with the contact layer when no voltage is applied between the first and second electrodes.

The equal wettability of the fluid contact layer on both sides of the intersection allows a larger movement of the meniscus and, as a consequence, a greater change in curvature of the meniscus. It allows a concave meniscus to become convex or vice versa.

Accordingly, in a first broad form, the present invention relates to fluid-focussed, accommodating lens that is implanted in the eye of a patient as a replacement or prosthetic lens. A standard lens-removal and/or replacement procedure may be employed in this regard, that is, a phacoemulsification/extracapsular cataract extraction. This technique involves making an incision where the cornea and the sclera meet. Through this incision, two of the three structures of the lens (i.e. the hard nucleus and the soft cortex) are removed. The last structure, the lens capsule, is left in the eye to support the intraocular lens implant.

Where cataract extraction is required, phacoemulsification is generally employed. In this procedure, an ultrasonic probe is inserted into the incision and used to break up the nucleus and cortex tissue, where it is suctioned out by the probe.

After the lens tissue has been removed, the fluid-focussed, accommodating lens, is placed into the capsular bag of the lens. The same incision where the lens tissue was removed is enlarged slightly and used to place the fluid-focussed accommodating lens in the eye.

Any suitable securing device may be used to maintain the position of the fluid focussed, accommodating lens. This includes haptics that can be loops or plate-like (into which the lens is embedded). In the absence of adequate capsular support, intraocular lenses may be sutured transclerally or to the iris.

In a particularly preferred form, the securing device is a haptic. The haptic is a looping extension that helps anchor a fluid-focussed, accommodating lens that is inserted to replace the eye's natural lens during surgery. The haptic may be of any suitable size or dimension, and is suitably made from an appropriate, biocompatible material, such as poly(methyl methacrylate) (PMMA), polypropylene, acrylic or silicone.

The fluid-focussed, accommodating lens has a focal length that is controlled by way of communication with range finding or autofocusing devices, designed to detect the distance of an object of regard from the lens.

In this embodiment, the components of the range finder or autofocusing device may be internal to the eye, external to the eye, or have components may be both internal and external to the eye.

The sensor is an autofocusing sensor, either a charge coupled device (CCD) or a complementary metal oxide semiconductor (CMOS). In this embodiment, the autofocusing sensor adjusts automatically by way of photon distribution in an optical pathway of the eye of the patient, with the autofocusing sensor providing input to algorithms that compute the contrast of the object/s in the visual pathway. Suitable autofocusing sensors include those that are used for automatically setting the focus of cameras by way of passive autofocus.

The controller of the range finder is in electrical communication with the power source, to provide a range of intensities of electrical signals that can be delivered through to the fluid-focussed, accommodating lens. Preferably, the controller is adjustable, such as by way of radio-frequency signals.

The power source for the lens system, which preferably comprises at least two electrodes, may take the form of a long-life battery or a rechargeable battery. The battery may be internal to the eye, or external to the eye. Where an internal rechargeable battery is used, transcorneal transfer of power through the cornea can be achieved through electromagnetic induction. At least two coils are required, a primary coil external to the eye and a secondary coil implanted within the eye of the patient. The primary and secondary coils are positioned so that they are inductively coupled. The primary coil is energized with a time-varying current, and thus a time-varying magnetic flux can be produced by the primary coil. When the secondary coil is appropriately oriented and in proximity to the primary coil, a time-varying magnetic flux induces a time-varying current within the secondary coil, according to Faraday's principle of electromagnetic induction.

In one form, the range finder is provided by two semicircular structures that are attached to the periphery of the optical zone of the fluid-focussed, accommodating lens. Preferably, the first semicircular structure contains one or more autofocusing sensors and is located and attached inferiorly of the fluid-focussed, accommodating lens, in the inferior 180° of the diameter of the lens. Even more preferably, the second semicircular structure is attached to the superior 180° diameter of the fluid-focussed, intraocular lens and contains a power source such as a battery, and a controller for modulating an electrical current that is delivered to the fluid-focussed, accommodating intraocular lens. Electrical coupling of the components of the range finder and the fluid-focussed, accommodating intraocular lens can be performed during an initial surgical procedure to insert the lens, prior to closure of an incision in the limbus.

Alternatively, the range finder is inserted into the patient's eye after the fluid-focussed, accommodating lens has been placed into the eye, so the position of the replacement lens has an opportunity to adjust in the post-operative period, as a result of fibrosis occurring in the lens capsule.

In a preferred form, further, post-operative adjustments to the focal length of the lens may be made post-surgically, such as by way of delivery of radio-frequency signals to the control unit of the range finder.

In another broad form, the fluid-focussed, accommodating lens may be formed into a contact lens. In this form, the lens has a total diameter of a range of around 9 to 12 millimeters.

Preferably, the outer 2 millimeters of the lens comprise a range finder, the range finder comprising a power source, a control unit and at least one autofocusing sensor.

The contact lens may be positioned in a patient's eye using standard ballasting techniques for contact lens. Preferably, the ballasting technique allows the power source and the control unit of the range finder to sit superiorly, and the at least one autofocusing sensor to sit inferiorly, when the contact lens is in situ in the patient's eye.

In yet another broad form, the fluid-focussed, accommodating lens may be as eyeglasses. In this embodiment, the lens diameter required is in an approximate range of 30-60 mm. The above-discussed components of the range finder, which are required for the intraocular lens, would also be required when the fluid-focussed lens is employed in spectacles. However, the placement of the components of the range finder can vary considerably in this embodiment, as the lens is not employed in or on the eye, and as such, may be placed, for example, in or on the rim of the spectacles, or worn as an item of jewelry.

In order that the invention may be readily understood and put into practical effect, particular preferred embodiments will now be described by way of the following non-limiting examples.

Persons skilled in the art will appreciate that numerous variations and modifications will become apparent. All such variations and modifications which become apparent to persons skilled in the art, should be considered to fall within the spirit and scope that the invention broadly appearing before described.

EXAMPLE 1

Insertion of a Fluid-Focussed Accommodating Intraocular Lens into a Cataractous Eye The lens has similar dimensions to a standard intraocular lens with a 4-6 mm optical zone. Fixation of the lens within the capsular bag is by way of two haptics that hold and centre the lens in the capsular bag (the capsular bag being approximately 10 mm in diameter).

As the fluid-focussed, accommodating lens is not foldable, it is inserted through a larger corneo-limbal incision than is ordinarily required in lens replacement procedures. This incision is made in the standard cataract extraction, and an ophthalmic viscosurgical device (OVD) (i.e. a biocompatible, transparent, space maintaining gel) is inserted into the anterior chamber to maintain space and to protect the corneal endothelium. A central circular opening is made in the anterior lens capsule (capsulorhexis) of 4-6 mm diameter and the content of the lens (the cataractous portion) is removed by standard phacoemulsification techniques.

Viscoelastic (OVD) is injected to reinflate the capsular bag and the lens is inserted into the space within the capsular bag. At this point, two semicircular structures (up to 2 mm in width) are inserted that attach to the periphery of the optical zone of the intraocular lens. The first of these is inserted so that it lies inferiorly and contains one or more autofocusing sensors. These are located inferiorly so that they are not obstructed by the eyelid (the superior eyelid overlaps the superior iris/cornea). As these autofocusing sensors would underlie the iris, post-operatively, an aperture is made in the iris, either surgically or with a YAG laser—this procedure is delayed so that the final position of the lens/sensors has stabilized (the position of the lens can change in the post-operative period as a result of fibrosis in the lens capsule).

The second semicircular component that sits along the superior aspect of the lens optic is a power source and controller that can either be a long-term (i.e. long-life) battery that could be replaced or be recharged via induction (as for cochlear implants). Electrical coupling of these components would be carried out and the device tested prior to closure of the incision in the limbus. The viscoelastic is removed and subconjunctival antibiotics and anti-inflammatory agents injected and the eye dressed.

In the post-operative period, final adjustments to the device are carried out by radiofrequency signals to the control unit to set the power of the lens for the individual eye as well as the range of required focusing power.

EXAMPLE 2

Contact Lens

The lens design is similar to the intraocular lens design but with a larger diameter to conform with standard contact lens dimensions. The overall diameter is 9-12 mm, with the outer 2 mm containing a range finder that sits inferiorly (and kept in this position by a ballasting mechanism that is occasionally utilized in contact lens design). The battery/controlling unit sits superiorly. The lens is similar in thickness to an aphakic contact lens of approximately 2 mm centrally. It is worn on a daily wear basis.

What is claimed is:

1. A method of treating a vision disorder in a patient, comprising the placement of a fluid-focussed, accommodating intraocular lens (IOL) entirely within an eye of the patient, wherein the lens comprises:
   a substantially cylindrical fluid chamber having a cylinder wall and an axis, the fluid chamber including a first fluid and an axially displaced second fluid, the fluids being non-miscible and having different indices of refraction,
   a fluid contact layer where the first fluid and the second fluid contact each other so as to form a meniscus that functions as a lens, said fluid contact layer arranged on the inside of the cylinder wall,
   a first electrode separated from the first fluid and second fluid by the fluid contact layer,
   a second electrode acting on the second fluid,
   a range finder placed in communication with the fluid-focussed, accommodating lens, the range finder including at least an autofocusing sensor and a power source, the range finder controlling the focal length of the lens,
   the fluid contact layer having a wettability by the second fluid which varies under the application of a voltage between the first electrode and the second electrode, such that the shape of the meniscus varies in dependence on the voltage,
   wherein the wettability of the fluid contact layer by the second fluid is substantially equal on both sides of the intersection of the meniscus with the contact layer when no voltage is applied between the first and second electrodes,
   the method comprising the steps of:
   removing the content of the lens capsule of the eye of the patient;
   placing the fluid-focussed, accommodating intraocular lens inside a capsular bag of the eye of the patient;
   fixating the fluid-focussed, accommodating intraocular lens within the capsular bag by way of a securing device that holds and centers the fluid-focussed, accommodating intraocular lens in the capsular bag; and
   manipulating the application of voltage in order to change the radius of curvature in the meniscus and thereby the focal length of the lens.

2. The method according to claim 1, wherein the lens is inserted into the capsular bag through a first aperture made by an incision into the eye.

3. The method according to claim 2, wherein the incision into the eye is a corneo-limbal incision.

4. The method according to claim 1, wherein an anterior chamber of the eye is maintained by way of an ophthalmic viscoelastic device (OVD).

5. The method according to claim 4, wherein the viscoelastic device is inserted into the anterior chamber of the eye, where it maintains a space inside the anterior chamber, and protects the corneal endothelium.

6. The method according to claim 1, wherein an opening is made in the lens capsule.

7. The method according to claim 6, wherein the opening in the lens capsule is a capsulorhexis incision.

8. The method according to claim 7, wherein the capsulorhexis incision is 4-6 mm in diameter.

9. The method according to claim 1, wherein the content of the lens capsule is removed by way of a phacoemulsification technique.

10. The method according to claim 1, wherein an OVD viscoelastic substance is injected into the capsular bag, thereby reinflating the capsular bag.

11. The method according to claim 1, wherein the securing device is at least one haptic.

12. The method according to claim 1, wherein the range finder is part of the fluid-focussed, accommodating.

13. The method according to claim 1, wherein the range finder is placed external to the eye.

14. The method according to claim 1, wherein the range finder has components that are internal and external to the patient's eye.

15. The method according to claim 1, wherein the range finder is provided by first and second semicircular structures that attach to a peripheral region of an optical zone of the fluid-focussed, accommodating lens.

16. The method according to claim 15, wherein the first semicircular structure contains the at least one autofocusing sensor.

17. The method according to claim 15, wherein the first semicircular structure is located inferiorly of the fluid-focussed, accommodating lens.

18. The method according to claim 15, wherein the second semicircular component of the range finder provides the power source, and a control unit, the control unit controlling the amount of electrical current delivered to the fluid-focussed, accommodating lens.

19. The method according to claim 18, wherein the control unit is adjustable.

20. The method according to claim 19, wherein the control unit is adjustable by way of radiofrequency signals directed at the control unit.

21. The method according to claim 15, wherein, the second semicircular component of the range finder is placed along a superior aspect of the fluid-focussed, accommodating lens, according to an in situ position of the lens.

22. The method according to claim 1, wherein the range finder is inserted post-operatively of the fluid-focussed, accommodating lens.

23. The method according to claim 1, wherein the power source of the range finder is a battery.

24. The method according to claim 1, wherein electrical coupling of the range finder and the lens is performed prior to closure of a surgical incision for insertion of the range finder.

25. The method according to claim 24, wherein further adjustment of electrical coupling between the range finder and the fluid-focussed, accommodating lens is performed in a post-operative period to set the power of the lens for the patient's eye, further wherein the range of required focusing power of the lens is also adjusted.

* * * * *

UNITED STATES PATENT AND TRADEMARK OFFICE
CERTIFICATE OF CORRECTION

| | |
|---|---|
| PATENT NO. | : 8,216,306 B2 |
| APPLICATION NO. | : 11/332088 |
| DATED | : July 10, 2012 |
| INVENTOR(S) | : Minas Theodore Coroneo |

Page 1 of 1

It is certified that error appears in the above-identified patent and that said Letters Patent is hereby corrected as shown below:

In the Claims:

At column 10, line 65, in Claim 12, after "accommodating" please add --lens--.

Signed and Sealed this
Twenty-second Day of January, 2013

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,216,306 B2 |
| APPLICATION NO. | : 11/332088 |
| DATED | : July 10, 2012 |
| INVENTOR(S) | : Coroneo |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,552 days.

Signed and Sealed this
Seventeenth Day of May, 2016

Michelle K. Lee
*Director of the United States Patent and Trademark Office*